(12) United States Patent
Reisenhus

(10) Patent No.: US 11,357,921 B2
(45) Date of Patent: Jun. 14, 2022

(54) ACCESSORY DEVICE WITH PAIRING FEATURE

(71) Applicant: Novo Nordisk A/S, Bagsvaerd (DK)

(72) Inventor: Michael Bech Reisenhus, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 239 days.

(21) Appl. No.: 16/462,662

(22) PCT Filed: Dec. 5, 2017

(86) PCT No.: PCT/EP2017/081496
§ 371 (c)(1),
(2) Date: May 21, 2019

(87) PCT Pub. No.: WO2018/104292
PCT Pub. Date: Jun. 14, 2018

(65) Prior Publication Data
US 2019/0298932 A1    Oct. 3, 2019

(30) Foreign Application Priority Data

Dec. 5, 2016    (EP) ..................................... 16202204

(51) Int. Cl.
*A61M 5/315*    (2006.01)
*A61M 5/31*    (2006.01)
(Continued)

(52) U.S. Cl.
CPC .... *A61M 5/31568* (2013.01); *A61M 5/31553* (2013.01); *A61M 5/31583* (2013.01);
(Continued)

(58) Field of Classification Search
CPC .......... A61M 5/31568; A61M 5/31583; A61M 5/31553; A61M 5/20; A61M 2205/3592; A61M 2205/3306; A61M 2005/3126
See application file for complete search history.

(56) References Cited

U.S. PATENT DOCUMENTS

| 5,651,775 | A | * | 7/1997 | Walker | A61M 5/31533 |
| | | | | | 604/207 |
| 2001/0056258 | A1 | * | 12/2001 | Evans | G16H 20/17 |
| | | | | | 604/131 |

(Continued)

FOREIGN PATENT DOCUMENTS

| CA | 2773575 A1 | 10/2012 |
| EP | 2692378 A1 | 2/2014 |

(Continued)

*Primary Examiner* — Nathan R Price
*Assistant Examiner* — Tasnim Mehjabin Ahmed
(74) *Attorney, Agent, or Firm* — Wesley Nicolas

(57) ABSTRACT

A method of verifying that a first unit and a second unit being mounted to each other are correctly paired, the first unit comprising a first visual identifier and the second unit comprising a second visual identifier, the method comprising the steps of (i) capturing an image of the first and second unit mounted to each, the image comprising both the first and the second visual identifier, and (ii) processing the captured image to (a) identify the first and the second visual identifier, and (b) determine whether the captured identifiers represent a predefined combination of visual identifiers to thereby verify the pairing.

11 Claims, 5 Drawing Sheets

(51) Int. Cl.
  *H04W 4/80* (2018.01)
  *A61M 5/20* (2006.01)
(52) U.S. Cl.
  CPC ....... *A61M 5/20* (2013.01); *A61M 2005/3126* (2013.01); *A61M 2205/3306* (2013.01); *A61M 2205/3561* (2013.01); *A61M 2205/3569* (2013.01); *A61M 2205/3592* (2013.01); *A61M 2205/52* (2013.01); *A61M 2205/6063* (2013.01); *A61M 2205/6072* (2013.01); *A61M 2205/6081* (2013.01); *H04W 4/80* (2018.02)

(56) References Cited

U.S. PATENT DOCUMENTS

| | | |
|---|---|---|
| 2009/0318865 A1 | 12/2009 | Moller et al. |
| 2015/0164606 A1 | 6/2015 | Jacobs et al. |
| 2018/0028760 A1* | 2/2018 | Gugl .................. A61M 5/3157 |

FOREIGN PATENT DOCUMENTS

| | | |
|---|---|---|
| EP | 3058973 A1 | 8/2016 |
| WO | 01/70304 A1 | 9/2001 |
| WO | 2010052275 A2 | 5/2010 |
| WO | 2013120776 A1 | 8/2013 |
| WO | 2014161952 A1 | 10/2014 |
| WO | 2015185687 A1 | 12/2015 |
| WO | 2016135236 A1 | 9/2016 |

* cited by examiner

ACCESSORY DEVICE WITH PAIRING FEATURE

CROSS-REFERENCE TO RELATED APPLICATIONS

This application is a 35 U.S.C. § 371 National Stage application of International Application PCT/EP2017/081496 (published as WO 2018/104292), filed Dec. 5, 2017, which claims priority to European Patent Application 16202204.0, filed Dec. 5, 2016, the contents of all above-named applications are incorporated herein by reference.

The present invention generally relates to medical devices for which the generation, collecting and storing of data are relevant. In specific embodiments the invention relates to devices and systems for capturing and organizing drug delivery dose data in a reliable and user-friendly way.

BACKGROUND OF THE INVENTION

In the disclosure of the present invention reference is mostly made to drug delivery devices comprising a threaded piston rod driven by a rotating drive member, such devices being used e.g. in the treatment of diabetes by delivery of insulin, however, this is only an exemplary use of the present invention.

Drug delivery devices have greatly improved the lives of patients who must self-administer drugs and biological agents. Drug delivery devices may take many forms, including simple disposable devices that are little more than an ampoule with an injection means or they may be durable devices adapted to be used with prefilled cartridges. Regardless of their form and type, they have proven to be great aids in assisting patients to self-administer injectable drugs and biological agents. They also greatly assist care givers in administering injectable medicines to those incapable of performing self-injections.

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, and the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable to automate the logging of injection information from medication delivery systems.

Though some drug delivery devices integrate this monitoring/acquisition mechanism into the device itself, e.g. as disclosed in US 2009/0318865 and WO 2010/052275, most devices of today are without it. The most widely used devices are purely mechanical devices being either durable or prefilled. The latter devices are to be discarded after being emptied and so inexpensive that it is not cost-effective to build-in electronic data acquisition functionality in the device it-self. Addressing this problem a number of solutions have been proposed which would help a user to generate, collect and distribute data indicative of the use of a given medical device.

For example, WO 2013/120776 describes an electronic supplementary device (or "add-on device") adapted to be releasably attached to a drug delivery device of the pen type. The device includes a camera and is configured to perform optical character recognition (OCR) on captured images from a rotating scale drum visible through a dosage window on the drug delivery device, thereby to determine a dose of medicament that has been dialed into the drug delivery device. A further external device for a pen device is shown in WO 2014/161952. As the external device is designed to detect signals or events originating from the device to which it is attached it is important that the two devices are correctly positioned relatively to each other to ensure proper operation and prevent incorrect measurements. WO 2016/135236 discloses an accessory device adapted to ensure that the accessory device is correctly mounted on a drug delivery, the two devices comprising corresponding mechanical coding structures, and WO 2015/185687 discloses a logging device adapted to cope with situations in which the logging device has been turned off automatically.

Having regard to the above, it is an object of the present invention to provide devices and methods allowing secure, easy and cost-effective operation of a drug delivery assembly comprising a user-mountable add-on device.

DISCLOSURE OF THE INVENTION

In the disclosure of the present invention, embodiments and aspects will be described which will address one or more of the above objects or which will address objects apparent from the below disclosure as well as from the description of exemplary embodiments.

Thus, in a first general aspect of the invention a method is provided for verifying that a first unit and a second unit that have mounted to each other are correctly paired, the first unit comprising a first visual identifier and the second unit comprising a second visual identifier, the method comprising the steps of (i) capturing an image of the first and second unit mounted to each, the image comprising both the first and the second visual identifier, and (ii) processing the captured image to identify the first and the second visual identifier, and determine if the captured identifiers represent a predefined combination of visual identifiers to thereby verify the pairing.

In a more specific aspect of the invention a method of pairing a combination of a drug delivery device and an add-on device with an external control device is provided. The method comprises the steps of providing a drug delivery device, an add-on device and a control device. The drug delivery device comprises a first visual identifier. The add-on device comprises communication means allowing the add-on device to communicate with an external control device, and a second visual identifier, wherein the add-on device is adapted to be releasably mounted on and in engagement with the drug delivery device, wherein the add-on device is adapted to capture dose related data from a drug delivery device when mounted thereon, and wherein the add-on device is adapted to receive a pairing confirmation from the external control device, whereby the add-on device is actuated from an un-paired to a paired mode. The control device comprises image capturing means, processor means, storage means comprising information in respect of at least one predefined combination of a first and a second visual identifier, and communication means allowing the control device to communicate with the add-on device. The method comprises the further steps of mounting the add-on device on the drug delivery device, capturing an image of the add-on device mounted on the drug delivery device, the image comprising both the first and the second visual identifier, processing the captured image to (i) identify the first and the second visual identifier, and (ii) determine if the captured identifiers represent a predefined combination of visual identifiers, and if it is determined that the captured identifiers represent a predefined combination, transmitting a paring confirmation from the control device to the add-on device, thereby actuating the add-on device from the un-paired to the paired mode.

By this arrangement the method utilizes the capabilities of an external device to verify correct mounting and pairing of two corresponding units, the external device being adapted to capture and analyse images. In this way a safe and cost-effective pairing and verification method is provided. The external device may e.g. be in the form of a smartphone or tablet computer running an app providing the described functionality, e.g. an iOS or Android device.

The drug delivery device may be in the form of device adapted to expel an amount of fluid drug from a cartridge, e.g. of the type traditionally used for subcutaneous administration of drugs for treatment of diabetes or for administration of growth hormone. Alternative the drug delivery device may be in the form of an inhalation device for the metered distribution of powder or an aerosol to the lungs of a patient.

In an exemplary embodiment the add-on device is configured such that it cannot capture dose related data when in an un-paired mode, i.e. it is basically non-functional until actuated to its paired mode. The add-on device may be in the form of a logging device adapted to create and store a log of dose data on its own and/or create and store a log of dose data in combination with the external control device.

In an alternative configuration the add-on device can capture and store dose related data but cannot transmit the dose related data to the external control device. In this way dose data will not be lost in case the add-on device is not actuated to its paired mode, e.g. in case the user forgets to perform the pairing initially, or in case no corresponding external control device is at hand. In this way any collected dose related data is captured in the device but is not accessible to the user until the devices have been properly paired. The latter aspect is important as the data may not correctly represent dose data in case the two devices do not correspond to a predefined combination, e.g. the drug delivery device contains U100 insulin whereas the add-on device is configured to determine dose sizes for drug delivery device containing U200 insulin. When the two devices have been successfully paired the stored dose data can be transmitted to the control device. In case the add-on device is provided with a display, actuation to the paired mode could allow dose data to be displayed on the add-on device. In case the pairing process does not result in pairing of the two devices the stored data in the add-on device may be deleted, e.g. after the user by the external control device has been prompted to accept deletion.

In a simple version of the above-described method for pairing a combination of a first and a second unit with a control device, a mounting sensor is dispensed with. Correspondingly, the pairing process will have to be initiated by the user. To minimize the risk that the paired add-on device is transferred to a different type of drug delivery device without having been properly paired thereto, the add-on device may be provided with a counting feature which would turn the add-on device into a passive state after an amount of drug corresponding to a full cartridge, e.g. 300 IU, has been counted and until a new pairing has been performed. Alternatively, the add-on device may be provided with a de-mounting sensor, e.g. associated with a release member which has to be activated in order to release the add-on device from the drug delivery to which it is mounted.

The pairing process may be initiated directly from the external control device, i.e. with the external control device the user captures an image of the add-on device mounted on the drug delivery device, the image comprising both the first and the second visual identifier, after which the above-described additional steps are performed. Indeed, the add-on device will have to be in a pairing state allowing a paring confirmation to be received. To achieve this the add-on device may be in a permanent low-power pairing state, or the add-on device may comprise a mounting sensor adapted to detect when the add-on device has been mounted on a drug delivery device, activation of the mounting sensor turning the add-on device into a pairing state. Alternatively the add-on device may be turned into a pairing state manually, e.g. by means of a user activating a button. Further, to prevent mismatch between a given add-on device and external control device, the two devices may have paired in an initial set-up procedure before allowing activation initiated by the external control device.

Alternatively the pairing process may be initiated from the add-on device, i.e. after mounting the add-on device on the drug delivery device, a pairing request is transmitted from the add-on device to the control device, which may then prompt the user to capture a pairing image. In a simple version the user will manually actuate the add-on device to transmit a pairing request to the external control device. In a more advanced version the add-on device comprises a mounting sensor adapted to be activated when the add-on device has been mounted on the drug delivery device, wherein the pairing request is transmitted automatically or is allowed to be transmitted when the mounting sensor has been activated. In the latter case the user will have to manually actuate the add-on device to send a pairing request. In case the pairing is not successful, e.g. because the external control device is not within transmission reach or is not in a receiving state, the pairing request may be repeated later initiated either from the add-on device or from the external control device. To prevent mismatch between a given add-on device and external control device, the two devices may have paired in an initial set-up procedure before allowing activation initiated by the external control device.

When provided with a mounting sensor the add-on device may be actuated from the paired to the un-paired mode when the mounting sensor detects that the add-on device has been removed from engagement with the drug delivery device. Further, when the mounting sensor detects that the add-on device has been removed from engagement with the drug delivery device an un-pairing control instruction may be transmitted from the add-on device to the control device.

In an exemplary embodiment the storage means comprises information in respect of a plurality of predefined combinations of first and a second visual identifiers, each predefined combination being associated with a predefined operational state of the control device, the method comprising the further step of setting the control device in an operational state corresponding to a determined pre-defined combination of visual identifiers. In this way the adaptation of the combined system, i.e. comprising the drug delivery device, the add-on device and the external control device, to a specific combination of a drug delivery device and an add-on device (represented by the first and a second visual identifiers) is performed in the control device.

For example, in a drug delivery device comprising a U100 insulin each expelled unit of insulin may correspond to a given incremental movement, e.g. amount of rotation, of an indicator member, whereas in a drug delivery device comprising a U200 insulin each incremental movement will correspond to two units of insulin being expelled. As a further variation the internal gearing of the drug expelling mechanism may vary allowing more or less drug volume to be expelled per increment of rotation, e.g. as used in a half-increment device intended for children. A given add-on device may be configured to merely determine the amount of incremental movements, which for the same number of expelled insulin units will be different for the two devices. However, if the control device has been set in an operational state corresponding to a determined pre-defined combination of visual identifiers, the control device will be able to calculate and store the correct dose amount.

In an exemplary alternative embodiment the add-on device can be set in a plurality of operational states, each state corresponding to one of a plurality of drug delivery devices each comprising a corresponding first visual identifier, the method comprising the further step of transmitting a setting signal from the control device to the add-on device to set the add-on device in an operational state corresponding to a given identified first visual identifier. In this way the actual amount of expelled drug can be calculated in the add-on device without having to rely on further processing in the associated external control device, this allowing e.g. dose amount data to be transmitted to additional external units or to be displayed directly on the add-on device when provided with a display.

Thus, when a given device is set in a predefined operational state corresponding to a given determined pre-defined combination of visual identifiers it is adapted to correctly interpret the information gathered, e.g. the add-on device or the external control device is set-up to correctly determine dose amounts for a given drug based on the concentration of the drug. Correspondingly, the add-on device or the external control device may be set-up to display the actual name of drug contained in the drug delivery device.

The above-described add-on devices may be adapted to determine at least one of: the time (relative or absolute) of expelling a dose of drug, and the size of a set and/or expelled dose of drug.

The first and second visual identifiers may be in the form of a plurality of letters and/or numbers, e.g. a brand name, a barcode, e.g. linear or matrix, a colour, a symbol or combinations thereof. Alternatively the visual identifier may be in the form of a blinking indicator, e.g. a blinking LED or a blinking LCD/OLED segment on the add-on device which may be active for a given amount of time after having been activated, e.g. when the add-on device is mounted. Such a light source would communicate a code and may be considered visually more attractive than e.g. a barcode.

In an exemplary alternative embodiment of the method, the provided drug delivery device comprises means allowing a user to set a dose size of drug to be expelled, as well as an indicator element arranged to move during setting and/or expelling of a dose amount, the amount of movement being indicative of the size of the set and/or expelled dose amount, and the provided add-on device is adapted to determine the amount of movement of the indicator member during setting and/or expelling of a dose amount, the amount of movement for a given pre-defined combination allowing a dose amount of drug to be calculated.

The indicator member may be adapted to rotate relative to a housing during dose setting and/or dose expelling corresponding to an axis of rotation, the amount of rotation corresponding to the dose set and/or amount of drug expelled from a reservoir by the expelling means, the indicator member having an initial rotational position. Correspondingly, the add-on device is adapted to detect and register the amount of rotation.

In a further aspect of the invention an add-on device configured to be releasably mounted to a drug delivery device is provided. The drug delivery device comprises a housing, a drug reservoir or a compartment for receiving a drug reservoir, drug expelling means comprising a dose setting member allowing a user to set a dose amount of drug to be expelled, an indicator member adapted to move relative to the housing during dose setting and/or dose expelling, the amount of movement corresponding to the dose set and/or amount of drug expelled from a reservoir by the expelling means, the indicator member having an initial position, and a first visual identifier. The add-on device is adapted to determine, when mounted to a drug delivery device housing, an amount of movement of the indicator member relative to the housing, the add-on device comprising mounting means adapted to releasably mount the add-on device to the drug delivery device in a predetermined position and orientation, a mounting sensor adapted to be actuated between an off and an on state when the add-on device is being been mounted in the predetermined position and orientation on a drug delivery device, a second visual identifier, communication means allowing the add-on device to communicate with an external control device, wherein the add-on device has a first operational state, a second operational state and a third operational state. The add-on device is in the first operational state when the mounting sensor is in the off state, the add-on device is in the second operational state when the mounting sensor is in the on state without having received an actuation signal from the external control device, the add-on device is in the third operational state when the mounting sensor is in the on state after having received an actuation signal from the external control device, and when in the third state, the add-on device can determine an amount of movement of the indicator member relative to the housing and transmit data corresponding thereto to the external control device.

The drug delivery device may comprise an indicator member adapted to rotate relative to the housing during dose setting and/or dose expelling corresponding to an axis of rotation, the amount of rotation corresponding to the dose set and/or amount of drug expelled from a reservoir by the expelling means, the indicator member having an initial rotational position, and the add-on device may correspondingly be adapted to determine, when mounted to a drug delivery device housing, an amount of rotation of the indicator member relative to the housing.

In an exemplary embodiment the add-on device is configured such that it cannot determine an amount of movement of the indicator member relative to the housing when in the second state.

Alternatively the add-on device may be configured such that when in the second state it can determine an amount of movement of the indicator member relative to the housing but cannot transmit data corresponding thereto to the external control device.

The add-on device may be configured such that an activation request signal for the external device is transmitted from the add-on device when the mounting sensor is actuated from the off to the on state.

The add-on device may comprise the same additional features and functionalities as described above in respect of an add-on device provided as part of the described method.

The add-on device may be provided in combination with the above-described drug delivery device and/or external control device, the combinations forming assemblies in accordance with aspects of the invention.

In an alternative version of the above-described method for pairing a combination of a first and a second unit with a control device, one or both of the visual identifiers are replaced with a NFC tack allowing one or both of the devices to be identified by the NFC functionality of a correspondingly equipped control device.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as non-insulins such as GLP-1 and analogues thereof. In the description of exemplary embodiments reference will be made to the use of insulin, however, the described logging device could also be used to create logs for other types of drug, e.g. growth hormone.

BRIEF DESCRIPTION OF THE DRAWINGS

In the following embodiments of the invention will be described with reference to the drawings, wherein.

In the figures like structures are mainly identified by like reference numerals.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Figure 1A:
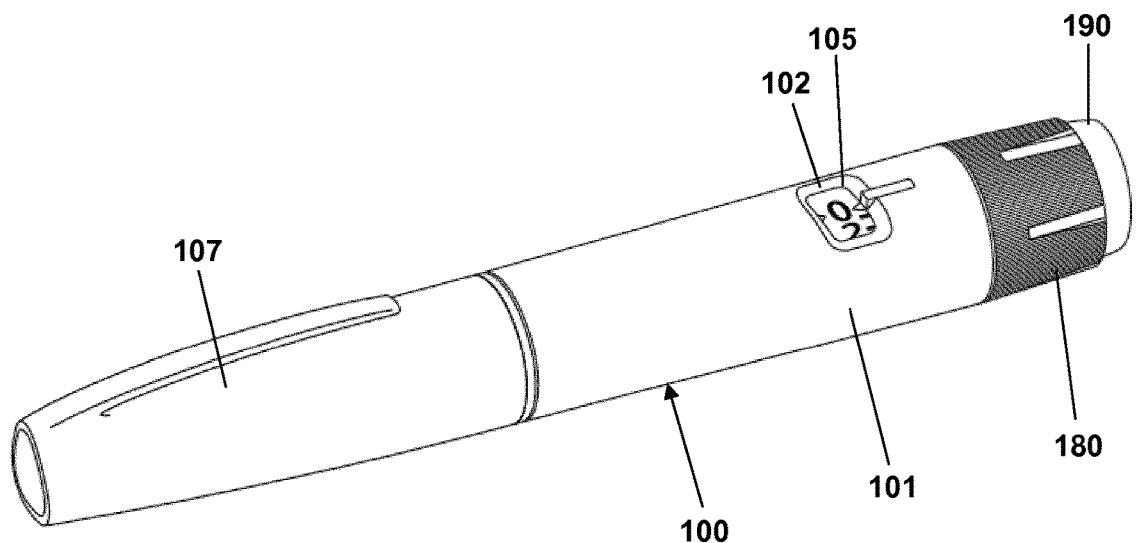
FIG. 1A shows a drug delivery device.

Before turning to embodiments of the present invention per se, an example of a prefilled drug delivery will be described, such a device providing the basis for the exemplary embodiments of the present invention. Although the pen-formed drug delivery device 100 shown in FIGS. 1A and 1B may represent a "generic" drug delivery device, the actually shown device is a Flex-Touch® prefilled drug delivery pen as manufactured and sold by Novo Nordisk A/S, Bagsværd, Denmark.

The pen device 100 comprises a cap part 107 and a main part having a proximal body or drive assembly portion with a housing 101 in which a drug expelling mechanism is arranged or integrated, and a distal cartridge holder portion 110 in which a drug-filled transparent cartridge 113 with a distal needle-penetrable septum is arranged and retained in place by a non-removable cartridge holder 110 attached to the proximal portion. The cartridge holder 110 comprises openings allowing a portion of the cartridge to be inspected, distal coupling means 115 allowing a needle assembly to be releasably mounted as well as proximal coupling means in the form of two opposed protrusions 114 allowing the cap 107 to be releasably mounted covering the cartridge holder 110. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug and which can then be expelled when the button 190 is actuated. The expelling mechanism comprises a helically rotatable scale drum member 105 with a plurality of indicia in the form of dose size numerals printed thereon, the dose size number corresponding to the currently set dose size being shown in display opening (or window) 102. Depending on the type of expelling mechanism embodied in the drug delivery device, the expelling mechanism may comprise a spring as in the shown embodiment which is strained during dose setting and then released to drive the piston rod when the release button is actuated. Alternatively the expelling mechanism may be fully manual in which case the dose member and the actuation button moves proximally during dose setting corresponding to the set dose size, and then is moved distally by the user to expel the set dose, e.g. as in a FlexPen® manufactured and sold by Novo Nordisk A/S.

Figure 1B:
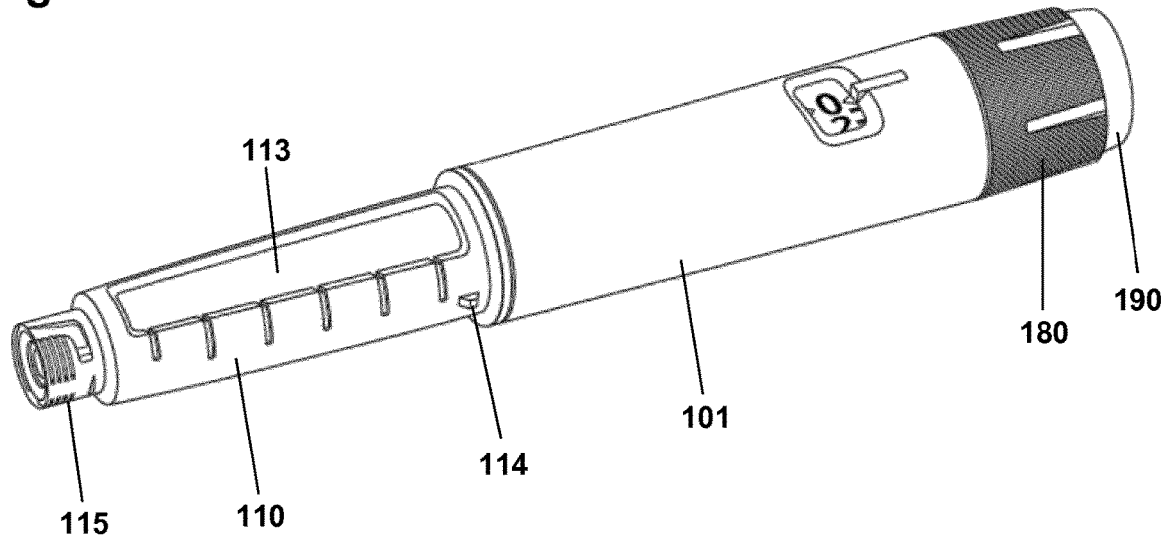
FIG. 1B shows the drug delivery device of FIG. 1A with the pen cap removed.

Although FIG. 1B shows a drug delivery device of the prefilled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

Figure 2A:
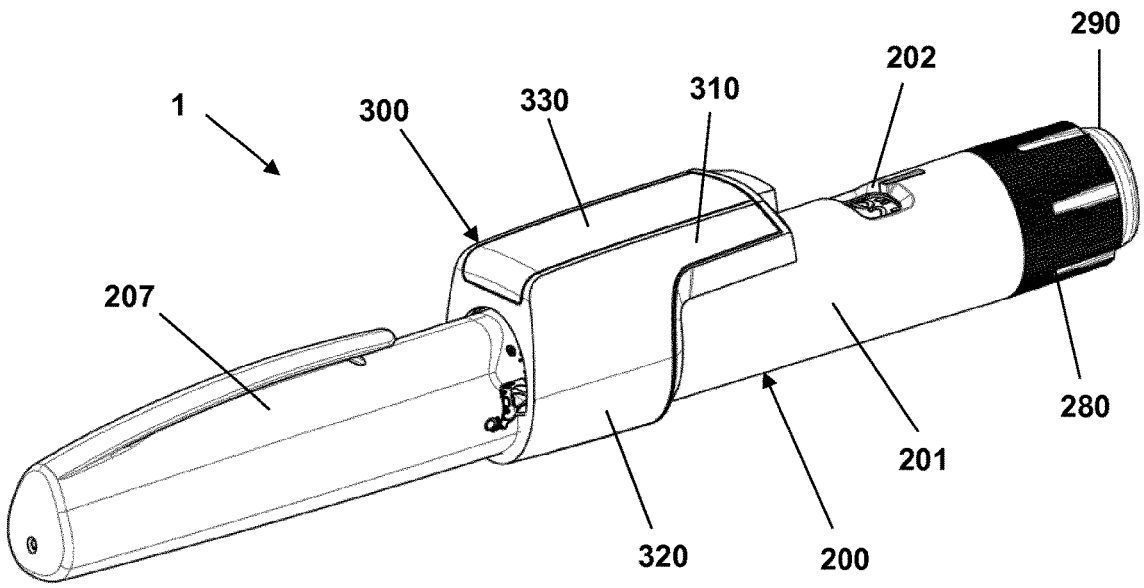
FIG. 2A shows an add-on device mounted on the housing of a drug delivery device.
Figure 2B:
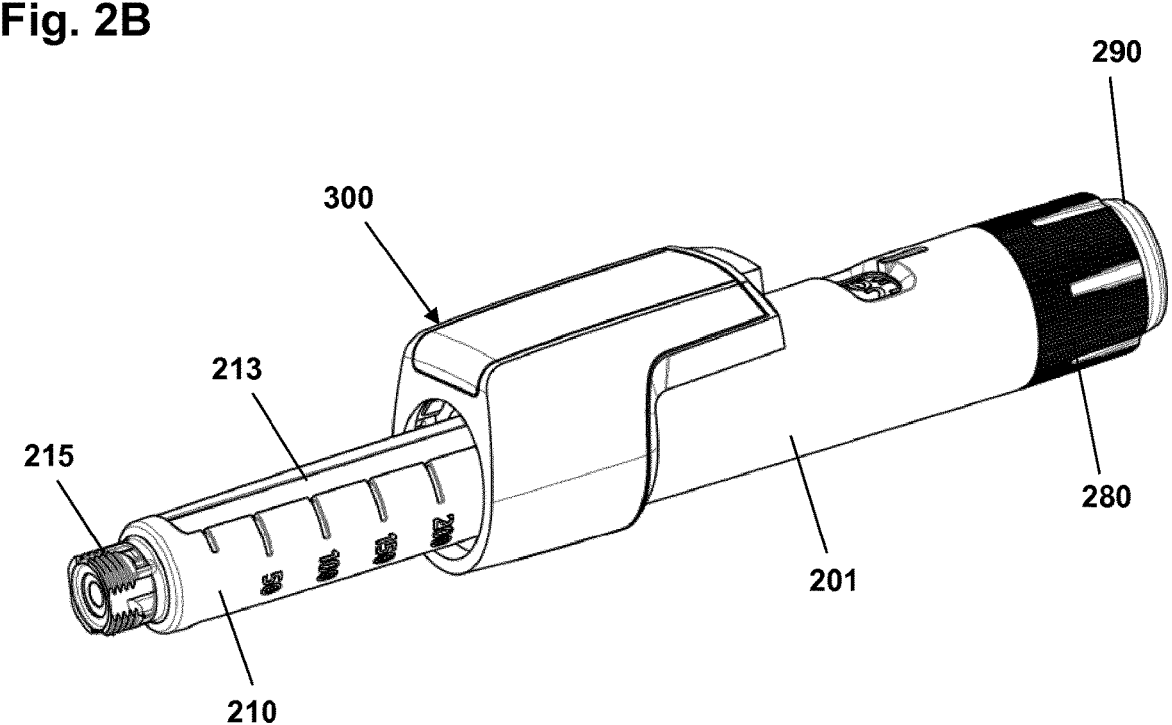
FIG. 2B shows the assembly of FIG. 2A with the pen cap removed.

FIGS. 2A and 2B show a drug delivery assembly 1 with a pen-formed drug delivery device 200 having a cartridge holder 210, the pen-formed drug delivery device 200 on which an electronic add-on logging device 300 is mounted. The drug delivery device generally corresponds to the above-described device 100, however, it has been modified internally to cooperate with the shown logging device such that the logging device is capable of registering events indicative of expelling activity, e.g. the amount of drug expelled during an expelling event.

Figure 3:
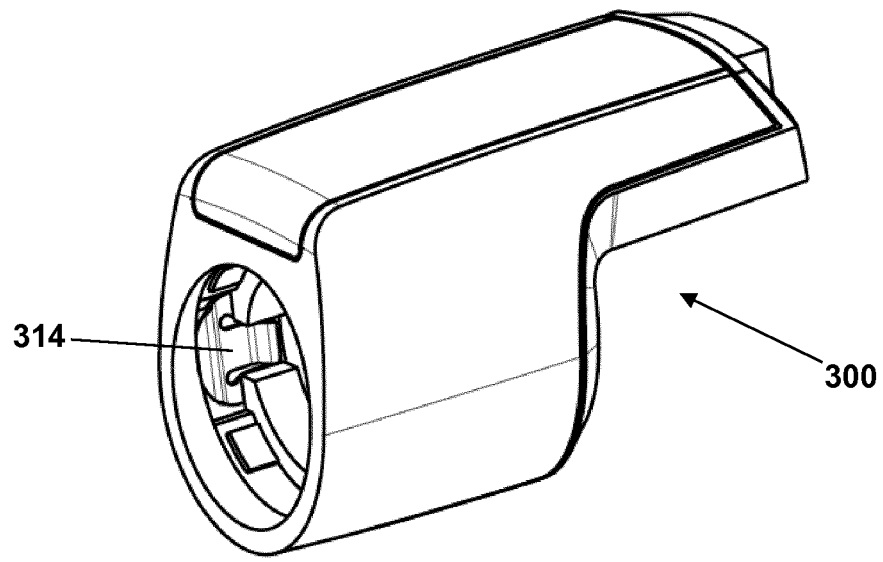
FIG. 3 shows the add-on device of FIG. 2A.

More specifically, the logging device 300 comprises a body portion 310 and a ring-formed portion 320 allowing the logging device to be mounted on a generally cylindrical pen device. The body portion comprises electronic circuitry and sensor means allowing a property to be detected representing an amount of drug being expelled from the cartridge, as well as a display 330 for displaying data to a user. The ring portion comprises coupling means allowing the logging device to be securely and correctly mounted on the pen body. The electronic circuitry and the sensor means may in part be arranged in the ring portion. FIG. 3 shows the logging device 300 before being mounted, the device comprising coupling means 314 adapted to engage corresponding protrusions 114 (see FIG. 1B) on the drug delivery device.

The logging device may be adapted to detect expelling activity in a number of ways, e.g. the logging device may be adapted to determine the size of an expelled and/or set dose by detecting sounds generated by the expelling mechanism during dose setting and/or dose expelling. The drug delivery device may be provided with a window or an opening allowing the logging device to optically detect motion of a component of the expelling mechanism. Alternatively the drug delivery device may be provided with electronic circuitry transmitting signals to be received by the logging device, e.g. by RF transmission.

In the shown embodiment the logging device comprises a sensor assembly adapted to measure magnetic fields. The drug delivery device is provided with an indicator element comprising a magnet moving together therewith, the magnet being configured to generate a spatial magnetic field which relative to the sensor assemblies varies corresponding to the spatial orientation of the magnet and thus the indicator element, thereby generating a spatial magnetic field which varies during movement of the indicator element, e.g. rotation during an expelling event. The logging device further comprises processor means configured to determine on the basis of measured values from the sensor assembly rotational movement of the indicator element on the basis of which the size of an expelled dose can be determined. A sensor is provided to detect whenever the add-on device is attached to or detached from a pen. A more detailed description of this concept is disclosed in WO 2014/161952.

Figure 4:
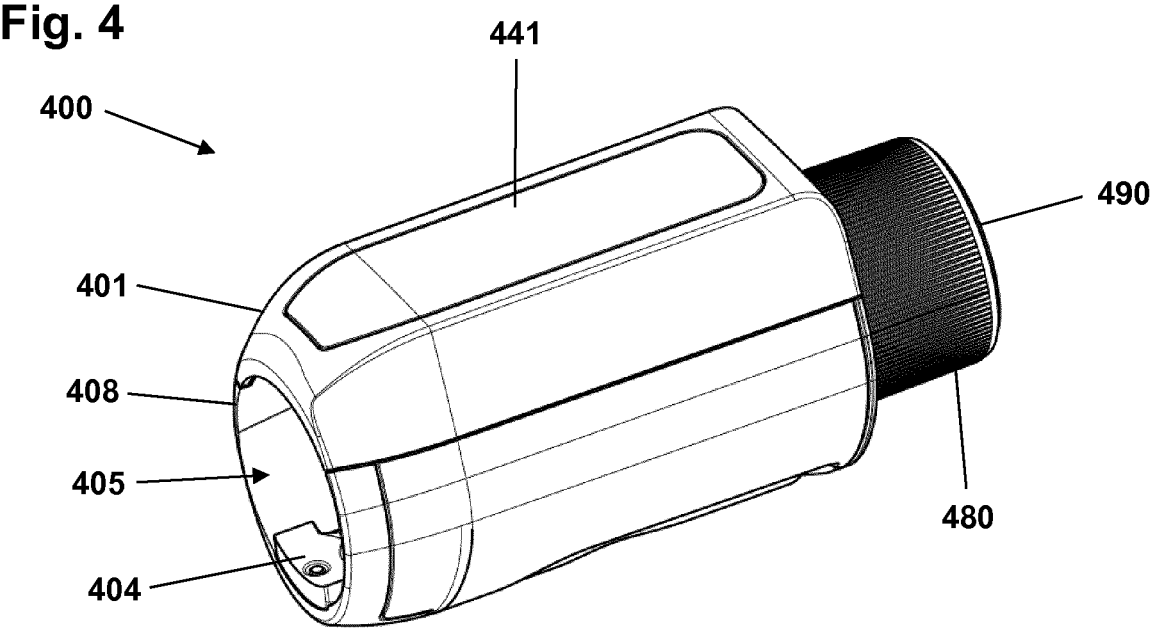
FIG. 4 shows a further embodiment of an add-on device adapted to be mounted on the housing of a drug delivery device.

FIG. 4 shows a further embodiment of an add-on device 400, the device comprising a housing 401, a display window 441, and proximally arranged user accessible add-on dial member 480 and user accessible add-on release button 490. The add-on device housing forms a bore 405 with a distally-facing opening 408 adapted to receive the generally cylindrical proximal portion of a pen device of the above-described type, the bore being defined by a generally cylindrical mounting surface adapted to face the pen device. A firm grip between the two structures is provided by a locking structure 404 on the add-on device adapted to engage the pen device and securing a firm grip. A sensor is provided to detect when the add-on device is mounted on or removed from a pen device.

The add-on device is adapted to determine the amount of drug expelled from the drug delivery device during an expelling event, i.e. the subcutaneous injection of a dose of drug. In the shown embodiment determination of an expelled dose of drug is based on determination of scale drum position at the beginning and at the end of the expelling event. To determine the rotational position of the scale drum the dose numerals as seen in the display opening/window 102, 202 may be captured and used, this allowing an unmodified pen device to be used. Actual determination of scale drum position may be performed using e.g. optical character recognition (OCR) or template matching. For the shown embodiment the add-on device covers the display window for which reason the current dose size shown in the display window has to be captured and displayed on the electronic display 441. Alternatively, the add-on device may be designed to allow the user to view the display window.

The add-on device 400 is provided with a user accessible add-on dial member 480 adapted to engage the pen dose setting member 180, and a user accessible add-on release button 490 adapted to engage the pen release button 190, this arrangement allowing sensors and switches to be incorporated in the add-on device for detecting motion of the dose setting member and the release button. A more detailed description of the add-on device 400 as well as logging devices based on scale drum image capture in general is disclosed in e.g. patent application EP 16171883.8.

Prefilled drug delivery devices, e.g. of the type described above with reference to FIGS. 1 and 2, will often be used as a platform device to be used in combination with different types of drugs, e.g. different types of drugs per se or the same type of drug in different concentrations as is the case for the FlexTouch® and FlexPro® family of devices from Novo Nordisk A/S. For different concentrations of the same drug the scale drum will typically be different just as for different types of drug the units of measurement may be different, e.g. "mg" for GLP-1 drugs instead of "IU" for insulin, resulting in a different scale drum. Correspondingly, if an add-on device can be mounted on drug delivery devices utilized for different types or concentrations of drug it is necessary that a given add-on device can only be used in combination with the drug for which it is intended (e.g. fast or long acting insulin) or, alternatively, adapt itself to the actual drug or concentration if necessary.

As disclosed in e.g. WO 2013/050535 a drug delivery device may be provided with an identifier allowing a corresponding add-on dose logging device to identify the type of device and thus the type of drug, e.g. a colour or a code, however, such a feature would most likely result in higher costs and a higher complexity of the add-on device. Alternatively a mechanical safeguard, i.e. mechanical coding, may prevent proper attachment of the add-on device onto a pen it is not intended for, however, this would require a number of different add-on devices just as the pen device may have to be modified. It could also be imagined that such a mechanical safeguard could be overridden with the use of excessive force.

Addressing the above issue, the present invention provides in different aspects a concept for safe and cost-effective pairing of an add-on device and a corresponding drug delivery device onto which the add-on device is mounted.

More specifically, the pairing concept is based on utilizing the capabilities of an external device to verify correct mounting and pairing of two corresponding unit, the external device being adapted to capture and analyse images. A typical device of this type is represented by a modern smartphone or tablet computer, such a device typically being provided with both a high-resolution camera and ample processing power for image analysis, as well as being adapted to run third-party software, e.g. in the form of "apps" downloaded to the device. The smartphone further typically comprises wireless means for receiving and transmitting data, e.g. Bluetooth® or NFC, as well as a relatively large high-resolution display suitable for display of data both in the form of text, numbers and graphs. Correspondingly, a smartphone can be adapted to receive data from the add-on device making the smartphone a suitable means for the user to view the data captured by the add-on device.

Figure 5:
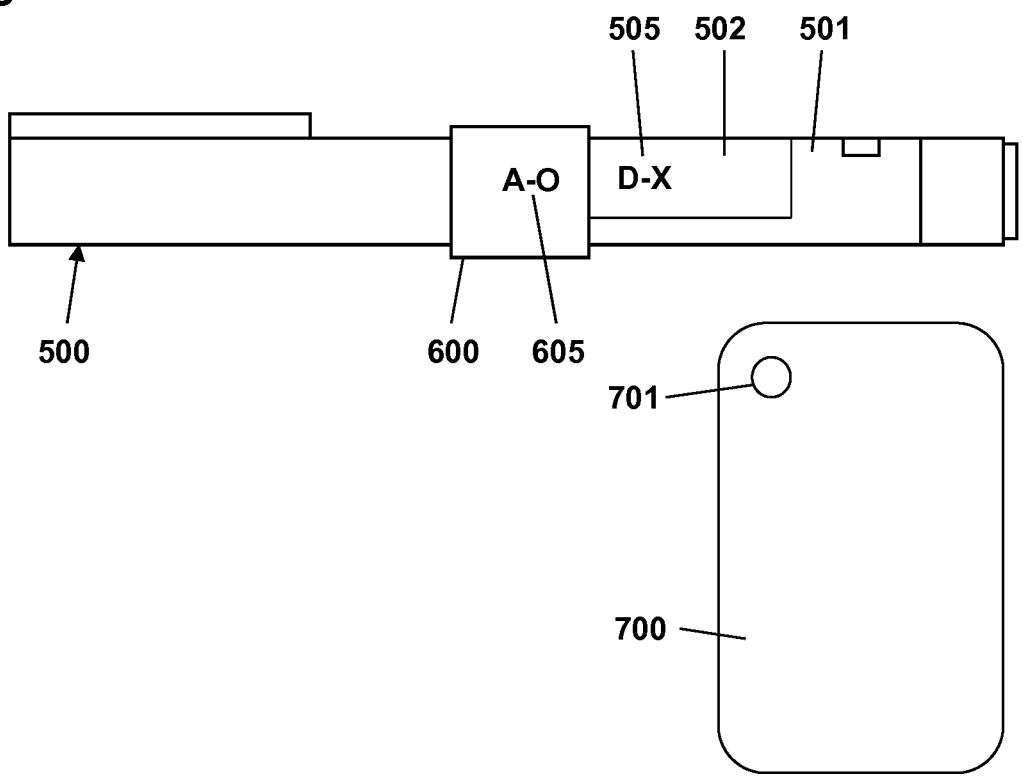
FIG. 5 shows a first embodiment of a system comprising a drug delivery device, an add-on device and an external device.

FIG. 5 discloses a first exemplary embodiment of a system adapted to implement aspects of the present invention. The system comprises a pre-filled drug delivery pen device 500 of the type described with reference to FIGS. 1 and 2, an add-on logging device 600 adapted to be mounted on the body housing 501, and an external control device in the form of a smartphone 700 provided with a camera 701.

The pen body housing is provided with a label 502 which typically is attached by adhesive means. The label comprises information identifying the drug formulation in the comprised cartridge. Part of the information will include the brand name, e.g. "D-X" as shown or Tresiba® marketed by Novo Nordisk A/S, which could be utilized as a unique visual identifier 505. The label may be a standard label or the label may be optimized for the present invention. The add-on device is adapted to be mounted on the pen device in a pre-defined rotational and axial position and comprises a mounting sensor adapted to detect that the add-on device has been correctly mounted. In the shown embodiment the add-on device is similar to the type shown in FIGS. 2 and 3 and thus adapted to be arranged centrally on the pen body. On an external surface the add-on device is provided with a visual identifier 605 which in the shown embodiment is the letters "A-O" but which for a commercial product could be in the form of a brand name which additionally may be written using a special graphic design. In addition or as an alternative a unique logo may be provided. As appears, the two visual identifiers are arranged in the vicinity of each other and oriented such that they can be captured by a smartphone camera device in a single picture.

Figure 6:
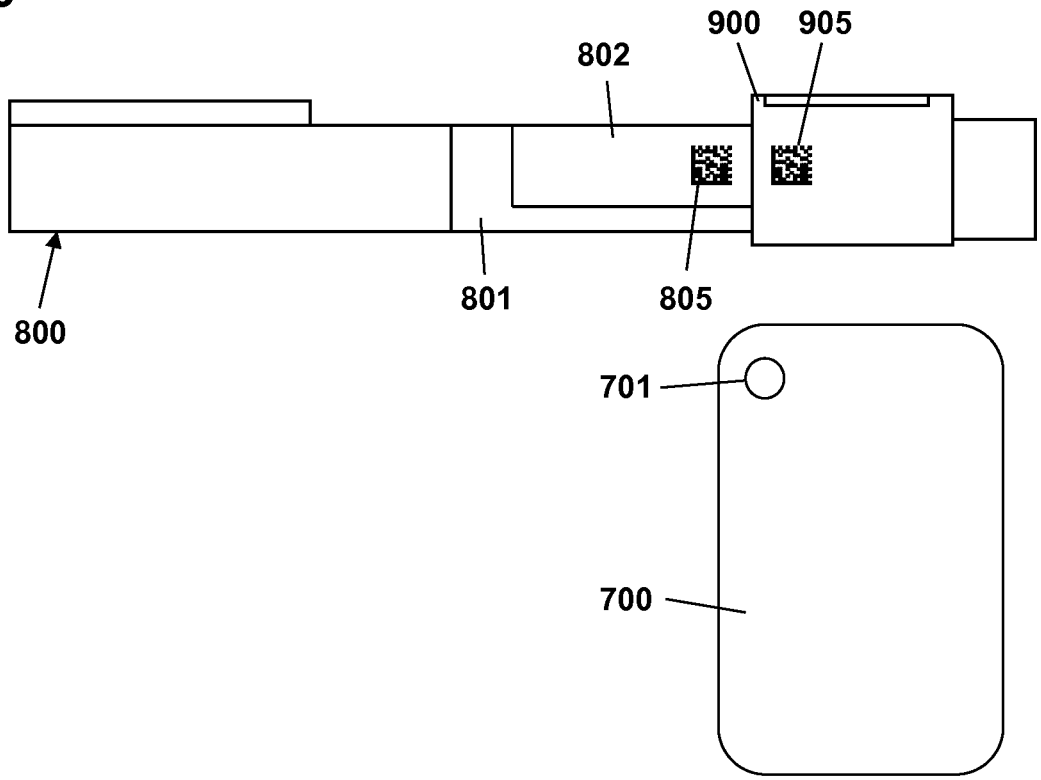
FIG. 6 shows a second embodiment of a system comprising a drug delivery device, an add-on device and an external device.

FIG. 6 discloses a second exemplary embodiment of a system adapted to implement aspects of the present invention. The system comprises a pre-filled drug delivery pen device 800 of the type described with reference to FIGS. 1 and 2, an add-on logging device 900 adapted to be mounted on the body housing 801, and a smartphone 700 provided with a camera 701.

The pen body housing 801 is provided with a label 802 which in the shown embodiment comprises a visual identifier 805 in the form of a barcode, e.g. a linear barcode or as shown a matrix (2D) code. The label may be a standard label comprising such a barcode or the label may be optimized for the present invention. The add-on device 900 is adapted to be mounted on the pen device in a pre-defined rotational and axial position and comprises a mounting sensor adapted to detect that the add-on device has been correctly mounted. In the shown embodiment the add-on device is similar to the type shown in FIG. 4 and thus adapted to be mounted proximally on the pen body covering the display opening. On an external surface the add-on device is provided with a visual identifier 905 which in the shown embodiment is matrix code. As appears, the two barcode identifiers are arranged in the vicinity of each other and oriented such that they can be captured by a smartphone camera device in a single picture.

In the shown exemplary embodiments of FIGS. 5 and 6 the two visual identifiers are of the same type, i.e. text or matrix codes, however, they could be used in any combination as long as they can identify the device on which they are arranged.

In an exemplary embodiment of the invention the two visual identifiers of an add-on device and the drug delivery device onto which it is mounted is used to either (i) verify that the two devices in a given configuration are compatible with each other, i.e. a given add-on device is adapted to only function with one specified type of pen device, or (ii) to control that the two devices will adapt to each other, i.e. typically the add-on device will adapt to the given pen type to which it is mounted.

Before a verification process for a given combination of an add-on device mounted on a drug delivery takes place, the add-on device and the external control device may have been paired during an initial set-up procedure, this uniquely linking the two devices to each other and allowing them to subsequently communicate with each other in a pairing process with a given drug delivery device.

The verification process could take place in a number of ways. For example, when the user attaches an add-on device provided with a mounting sensor to a corresponding pen device, the logging device mounting sensor will be actuated from the "off" to the "on" state indicating that the add-on device has been rotationally and axially correctly mounted on a corresponding pen device. Initiated by the actuated mounting sensor the add-on processor circuitry will emit a pairing request signal which can then be received by an external verification device, e.g. a smartphone provided with a camera and corresponding verification software (app). Alternatively the request may be initiated by the user, e.g. by activating a button. When the request has been received the external device will prompt the user to initiate the verification process, which may be explained and visualized on the external device display. The user will then capture a picture of the add-on device mounted on the pen and comprising both the pen device visual identifier and the add-on device visual identifier, which will then be processed by the verification software of the external device. The software will be adapted to identify one or more pre-defined pen device visual identifiers and one or more add-on device visual identifiers. The result of the image analysis may then be presented to the user on the external device display. If the identified combination of add-on device and pen device is an allowable combination the user will be asked to confirm the match before a pairing confirmation signal is transmitted to the add-on device. In case the add-on device is a multi-mode device adapted to work with two or more different pen devices the pairing confirmation signal may comprise mode setting instructions for the add-on device, e.g. for "Insulin× 100 IU/ml", however, before such a mode setting instruction is send from the external device the user is requested to accept the pairing. When the pairing confirmation/mode signal has been received by the add-on device a confirmation signal may be transmitted back to the external device which may then inform the user that the add-on device is operational and ready for use. During the verification process unique IDs may be exchanged between the two units.

Alternatively, the external device may be set in an operational state corresponding to a determined pre-defined combination of visual identifiers, this providing that a multi-use add-on device may be designed to simply capture the amount of rotational movement, the raw data then being stored and subsequently transmitted to the external device with a unique ID corresponding to the verified pairing. The received data will then be processed by the external device in accordance with the verified combination. Indeed, such a multi-mode add-on device would not be able to display dose size related values on a display, albeit it may display time related data.

When the pairing has been verified the add-on device will start detecting activity in the pen device, which data may then subsequently be transmitted to the external device, either automatically or upon request. The transmitted data may be coded such that it can only be retrieved by the external device performing the verification process. Correspondingly, the data may be coded to identify the specific add-on device. The transmitted data may be "raw" data or data processed by the add-on device.

When the add-on device mounting sensor becomes actuated from the "on" to the "off" state, typically when the add-on device is removed from the pen device, the verification status is cancelled and the add-on device will enter an unpaired state.

In case no pairing confirmation signal is received from an external device the mounted add-on device may suspend any data capture until a new verification process is initiated and finalized, e.g. when the add-on is mounted on a pen device anew. A new verification process may also be initiated from the external device. In case the add-on device is provided with a display the user may be notified accordingly.

Alternatively, the add-on device may start detect pen activity and store data in a protected log which may then subsequently be transmitted or made accessible when a verification process has successfully be performed. Otherwise the stored data may be deleted when the add-on device is removed from the pen device.

Figure 7:
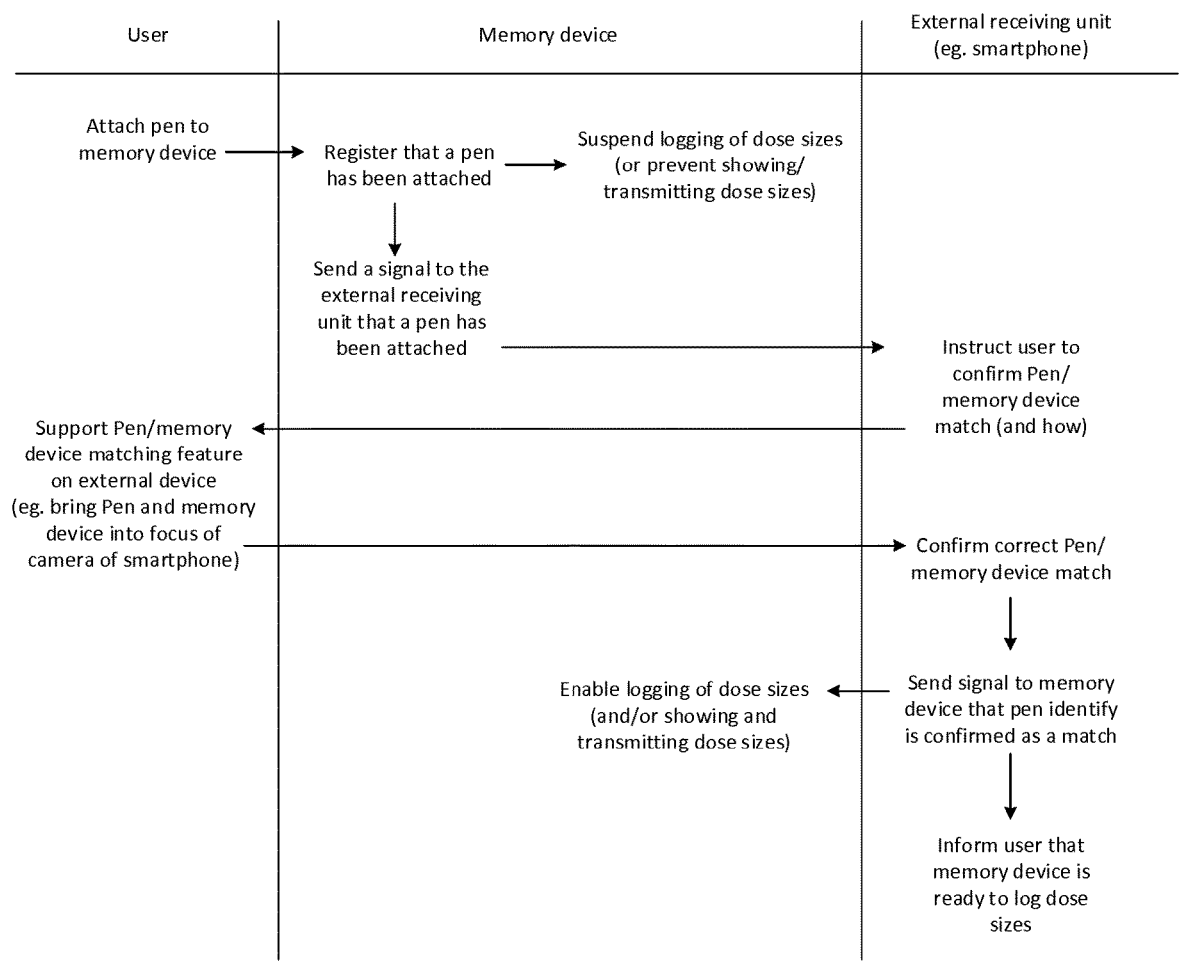
FIG. 7 shows a flow chart for an add-on verification process.

The significant process steps of the above-described exemplary verification process are summarized in the flow chart of FIG. 7.

In a further aspect of the invention an add-on device per se is provided, the device being specifically adapted to perform the above-described verification process. More specifically, an add-on device, e.g. of a type as shown in FIGS. 3 and 4, is configured to be releasably mounted to a drug delivery device as shown in FIGS. 5 and 6.

The add-on device is adapted to determine, when mounted to a drug delivery device housing, an amount of rotation of the indicator member relative to the housing. The add-on device comprises mounting means adapted to releasably mount the add-on device to the drug delivery device in a predetermined position and orientation, and may be provided with a mounting sensor adapted to be actuated between an off and an on state when the add-on device is being been mounted in the predetermined position and orientation on a drug delivery device, a visual identifier, communication means allowing the add-on device to communicate with an external control device.

Corresponding to the above-described verification process the add-on device has a first operational state, a second operational state and a third operational state, wherein the add-on device is in the first operational state when the mounting sensor is in the off state, the add-on device is in the second operational state when the mounting sensor is in the on state without having received an activation signal from the external control device, and the add-on device is in the third operational state when the mounting sensor is in the on state without having received an activation signal from the external control device. When in the third state, the add-on device can determine an amount of rotation of the indicator member relative to the housing and transmit data corresponding thereto to the external control device.

In the above-described embodiments the first visual identifier has been arranged on the drug delivery device pen housing per se, this corresponding to a disposable pre-filled drug delivery device in which a visual identifier arranged on the pen housing will be representative for the incorporated drug-filled cartridge. However, in alternative embodiments the above-described verification and activation process may be used for a durable device in which the first visual identifier is arranged on the replaceable drug cartridge.

For example, in the embodiment of FIG. 5 the shown drug delivery device may be of the durable type adapted to receive a replaceable cartridge in its cartridge holder, the first visual identifier being provided on the drug cartridge which then would have to be mounted in the cartridge holder such that the first visual identifier would be visual next to the add-on device. As the add-on device in the FIG. 5 embodiment is mounted on the pen corresponding to the interface between the pen main body portion and the cartridge holder, the add-on device may be provided with detection means adapted to detect when the cartridge holder is being removed, this making it possible to prevent that a cartridge is replaced without the combination of a first and second visual identifier being verified.

In the above description of preferred embodiments the add-on has been provided with a mounting sensor and the pairing process has been initiated from the add-on device, however, as described above in the disclosure of the present invention, the pairing process may alternatively be initiated from the external device. Correspondingly, as also outlined above, in simplified versions of the present invention, a mounting sensor can be dispensed with.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification.

The invention claimed is:

1. A method of pairing a combination of a drug delivery device and an add-on device with an external control device, comprising the steps of:
   providing the drug delivery device comprising a first visual identifier,
   providing an add-on device, comprising:
      communication structure allowing the add-on device to communicate with the external control device, and
      a second visual identifier,
      wherein the add-on device is adapted to be releasably mounted on and in engagement with the drug delivery device,
      wherein the add-on device is adapted to capture dose related data from the drug delivery device when mounted thereon,
      wherein the add-on device is adapted to receive a pairing confirmation from the external control device, whereby the add-on device is actuated from an un-paired mode to a paired mode, and
      a size of a set and/or expelled dose of drug,
   providing the external control device comprising:
      image capturing structure,
      processor structure,
      storage structure comprising information storage of predefined combinations of visual identifiers in respect of at least one predefined combination of the first visual identifier and the second visual identifier, and communication structure allowing the external control device to communicate with the add-on device, mounting the add-on device on the drug delivery device, capturing an image of the add-on device mounted on the drug delivery device with the external control device, the image comprising both the first visual identifier and the second visual identifier, processing the captured image to:
(i) identify the first visual identifier and the second visual identifier, and
(ii) determine if the captured identifiers represent at least one of the predefined combinations of visual identifiers, and if it is determined that the captured identifiers represent at least one predefined combination of visual identifiers, transmitting the pairing confirmation from the external control device to the add-on device, thereby actuating the add-on device from the un-paired mode to the paired mode.

2. A method as in claim 1, wherein in the un-paired mode the add-on device (i) cannot capture the dose related data from the drug delivery device on which it is mounted, or (ii) can capture and store the dose related data from the drug delivery device on which it is mounted but cannot transmit the dose related data to the external control device.

3. A method as in claim 1, wherein:
the add-on device comprises a mounting sensor adapted to be activated when the add-on device has been mounted on the drug delivery device, and
a pairing request is transmitted or is allowed to be transmitted when the mounting sensor has been activated.

4. A method as in claim 3, wherein the add-on device is actuated from the paired mode to the un-paired mode when the mounting sensor detects that the add-on device has been removed from engagement with the drug delivery device.

5. A method as in claim 3, comprising the further step of:
transmitting an un-pairing control instruction from the add-on device to the external control device when the mounting sensor detects that the add-on device has been removed from engagement with the drug delivery device.

6. A method as in claim 1, comprising the further steps of:
after mounting the add-on device on the drug delivery device, transmitting a pairing request from the add-on device to the external control device, and based on a received pairing request prompting a user to capture a pairing image.

7. A method as in claim 1, wherein:
the storage structure comprises information in respect of a plurality of predefined combinations of the first visual identifier and the second visual identifier comprising the at least one predefined combination of the first visual identifier and the second visual identifier, each predefined combination being associated with a pre-defined operational state of the external control device, the method comprising the further step of:
setting the external control device in an operational state corresponding to a determined pre-defined combination of visual identifiers.

8. A method as in claim 1, wherein:
the add-on device can be set in a plurality of operational states, each state corresponding to one of a plurality of drug delivery devices each comprising a corresponding first visual identifier, the method comprising the further step of:
transmitting a setting signal from the external control device to the add-on device to set the add-on device in an operational state corresponding to a given identified first visual identifier.

9. A method as in claim 1, wherein the add-on device is adapted to determine a time of expelling a dose of drug.

10. A method as in claim 1, wherein the first visual identifier or the second visual identifier is one of:
a plurality of letters and/or numbers,
a barcode,
a colour,
a symbol, and
a blinking signal.

11. A method as in claim 1, wherein:
the drug delivery device comprises structure allowing a user to set a dose size of drug to be expelled, as well as an indicator element arranged to move during setting and/or expelling of a dose amount, the amount of movement being indicative of the size of the set and/or expelled dose amount, and
the add-on device is adapted to determine the amount of movement of the indicator member during setting and/or expelling of the dose amount, the amount of movement for a given pre-defined combination allowing the dose amount of drug to be calculated.

* * * * *